(12) United States Patent
Naveed et al.

(10) Patent No.: US 10,335,159 B2
(45) Date of Patent: Jul. 2, 2019

(54) RELOADABLE MECHANICAL DEVICE FOR LIGATING LIVING TISSUE AND ACHIEVING HEMOSTASIS

(71) Applicant: BOSTON SCIENTIFIC SCIMED, INC., Maple Grove, MN (US)

(72) Inventors: Syed Naveed, Northborough, MA (US); Joshin Sahadevan, Bangalore (IN); Ramu Gangavenkatiah, Bangalore (IN); Gnaneswar Bangaru, Bangalore (IN); Manojkumar Rajanna, Bangalore (IN); Roopesh Kumar, Bangalore (IN)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 366 days.

(21) Appl. No.: 15/209,510

(22) Filed: Jul. 13, 2016

(65) Prior Publication Data

US 2017/0020531 A1  Jan. 26, 2017

Related U.S. Application Data

(60) Provisional application No. 62/194,555, filed on Jul. 20, 2015.

(51) Int. Cl.
*A61B 17/128* (2006.01)
*A61B 17/00* (2006.01)
(Continued)

(52) U.S. Cl.
CPC ...... *A61B 17/1285* (2013.01); *A61B 17/0057* (2013.01); *A61B 17/1222* (2013.01);
(Continued)

(58) Field of Classification Search
CPC ............ A61B 17/1222; A61B 17/1227; A61B 2017/0053; A61B 2017/00584; A61B 17/1285; A61B 17/0057
(Continued)

(56) References Cited

U.S. PATENT DOCUMENTS

| 2002/0045909 A1 | 4/2002 | Kimura et al. |
| 2005/0107809 A1* | 5/2005 | Litscher ............... A61B 17/122 |
| | | 606/142 |

(Continued)

FOREIGN PATENT DOCUMENTS

| DE | 299 01 599 | 5/1999 |
| DE | 10 2008 052 178 | 4/2009 |

(Continued)

*Primary Examiner* — Kathleen S Holwerda
(74) *Attorney, Agent, or Firm* — Fay Kaplun & Marcin, LLP

(57) ABSTRACT

A system for treating tissue includes a clip assembly including a pair of clip arms, each of the clip arms extending from a proximal end to a distal end, the proximal end of the clip arms connected to one another via a central member slidably received within a channel of a capsule to be moved between a tissue receiving configuration and a closed configuration, a cartridge for encasing the clip assembly including a groove formed therein to accommodate the clip assembly and an opening extending thereinto in communication with a portion of the groove such that the groove is open to an exterior of the cartridge via the opening, and an applicator releasably connectable to the clip assembly to move the clip assembly between the open and closed configurations, a distal portion of the applicator insertable through the opening of the cartridge to be connected to the clip assembly.

17 Claims, 6 Drawing Sheets

(51) Int. Cl.
*A61B 17/122* (2006.01)
*A61B 17/12* (2006.01)

(52) U.S. Cl.
CPC .. *A61B 17/1227* (2013.01); *A61B 2017/0053* (2013.01); *A61B 2017/00575* (2013.01); *A61B 2017/00584* (2013.01); *A61B 2017/00676* (2013.01); *A61B 2017/12004* (2013.01)

(58) Field of Classification Search
USPC ............ 606/139, 142, 143, 151, 157, 158
See application file for complete search history.

(56) References Cited

U.S. PATENT DOCUMENTS

| | | | |
|---|---|---|---|
| 2007/0112359 A1* | 5/2007 | Kimura | A61B 17/122 606/142 |
| 2009/0318937 A1* | 12/2009 | Matsuoka | A61B 17/1227 606/143 |
| 2013/0072947 A1 | 3/2013 | Terada | |
| 2014/0171974 A1* | 6/2014 | Zhu | A61B 17/122 606/144 |

FOREIGN PATENT DOCUMENTS

| | | |
|---|---|---|
| JP | 2008-289524 | 12/2008 |
| JP | 2009-125547 | 6/2009 |
| WO | 2015/059699 | 4/2015 |

\* cited by examiner

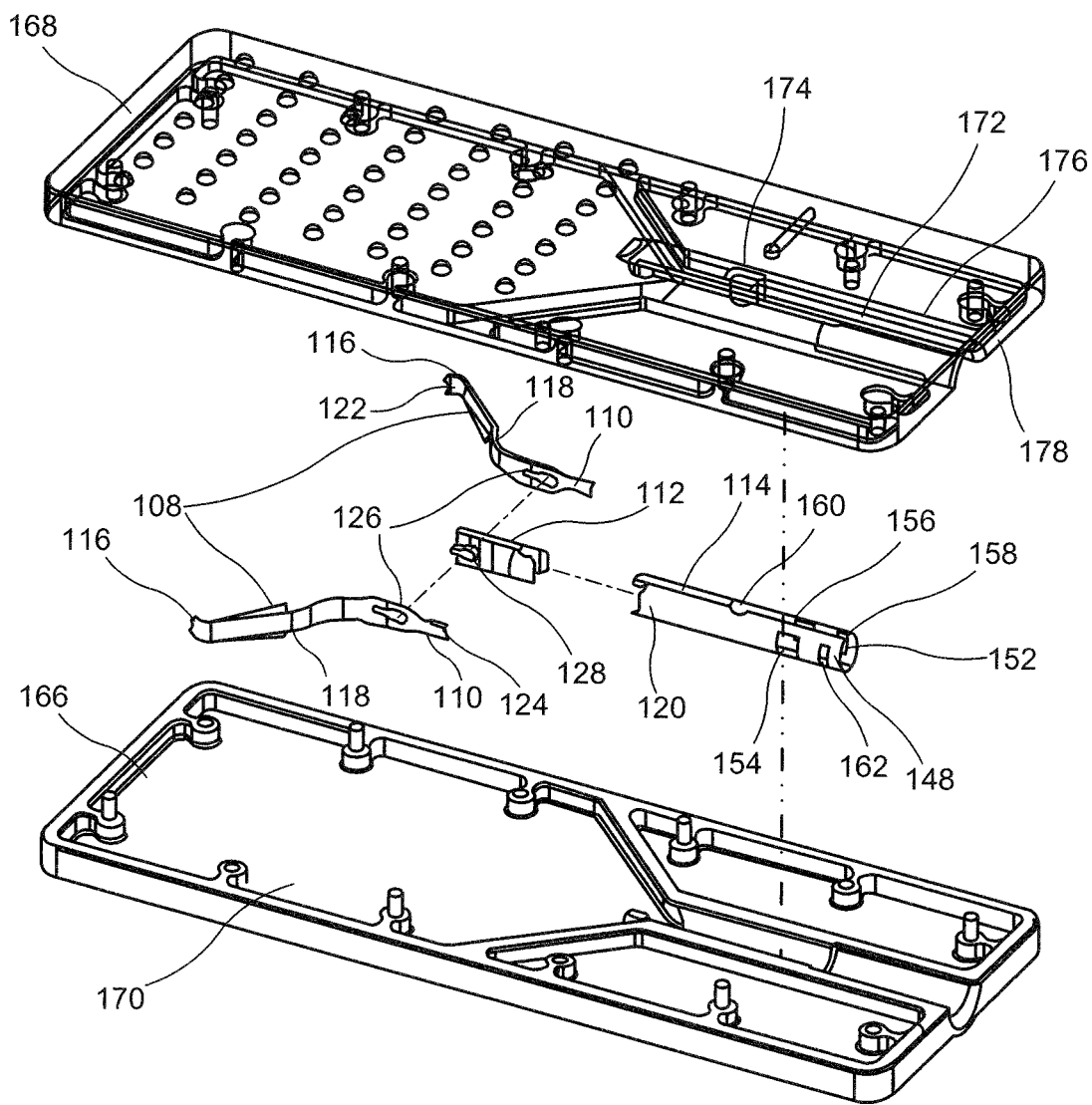
F I G. 2

RELOADABLE MECHANICAL DEVICE FOR LIGATING LIVING TISSUE AND ACHIEVING HEMOSTASIS

PRIORITY CLAIM

This application claims priority to U.S. Provisional Patent Application Ser. No. 62/194,555 filed Jul. 20, 2015; the disclosure of which is incorporated herewith by reference.

BACKGROUND

Many pathologies of the gastrointestional (GI) system, the biliary tree, the vascular system, and other body lumens and hollow organs are treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue, comprising a clip assembly including a pair of clip arms, each of the clip arms extending from a proximal end to a distal end, the proximal end of the clip arms connected to one another via a central member slidably received within a channel of a capsule to be moved between a tissue receiving configuration, in which distal ends of the clip arms are separated from one another, and a closed configuration, in which distal ends of the clip arms are moved toward one another, a cartridge for encasing the clip assembly including a groove formed therein to accommodate the clip assembly and an opening extending thereinto in communication with a portion of the groove such that the groove is open to an exterior of the cartridge via the opening, and an applicator releasably connectable to the clip assembly to move the clip assembly between the open configuration and the closed configuration, a distal portion of the applicator insertable through the opening of the cartridge to be connected to the clip assembly.

In an embodiment, the applicator may includes a flexible member extending longitudinally from a proximal end which, when the system is inserted into a living body, is external to the living body to remain accessible to a user, to a distal end including a connector mechanism for connecting to a proximal end of the capsule, a control member extending through the flexible member from a proximal end accessible to the user to an enlarged distal end releasably connectable to the central member.

In an embodiment, the central member may include a lateral slot extending therethrough, the lateral slot extending from an opening at the proximal end thereof to a distal portion, the proximal opening having a smaller cross-sectional area than the distal portion and the distal portion being sized and shaped to accommodate the enlarged end of the control member therein.

In an embodiment, the capsule may include a capsule slot extending laterally through a wall thereof longitudinally from the proximal end of the capsule to a distal end, the distal end being sized and shaped to permit passage of the enlarged end of the control member therethrough.

In an embodiment, the clip arms may be biased in the tissue receiving configuration.

In an embodiment, the capsule may include a locking window extending through a wall thereof for engaging an engaging tab at the proximal end of one of the clip arms to lock the clip arms in the closed configuration.

In an embodiment, the capsule may include engaging windows for receiving a portion of the connector mechanism of applicator.

In an embodiment, the connector mechanism may include a plurality of fingers biased radially outward to engage the connecting windows when the plurality of fingers are received within the channel of the capsule.

In an embodiment, the connector mechanism may further include a capsule release slidable over the plurality of fingers to be moved between a first configuration in which, when the plurality of fingers engage the engaging windows, the capsule release is mounted over the proximal end of the capsule to maintain the connection between the applicator and the clip assembly, and a second configuration in which the capsule release is slid proximally relative to the plurality of fingers to deform the fingers radially inward to release the fingers from the engaging windows.

In an embodiment, the applicator may include a handle member connected to the proximal end of the flexible member and a spool slidably mounted over the handle member and connected to the proximal end of the control member to move the control member longitudinally relative to the flexible member.

In an embodiment, the opening of the cartridge may be a slot extending therein laterally relative to a longitudinal axis of the clip assembly.

In an embodiment, the opening of the cartridge may extend therein in axial alignment with a longitudinal axis of the clip assembly.

The present disclosure also relates to a device for loading a clip assembly onto an applicator, comprising a cartridge for encasing a clip assembly including a groove extending therein, the groove sized and shaped to accommodate the clip assembly therein, and an opening extending into the cartridge in communication with a portion of the groove such that the groove is open to an exterior of the cartridge via the opening, the opening sized and shaped to permit passage of a connecting portion of an applicator therethrough.

In an embodiment, the opening may be a slot extending into the cartridge laterally relative to a longitudinal axis of the groove.

In an embodiment, the opening may extend into the cartridge in axial alignment with a longitudinal axis of the groove.

The present disclosure also relates to a method for loading a clip assembly onto an applicator, comprising inserting a distal portion of an applicator through an opening of a cartridge housing a clip assembly, the clip assembly housed within a groove extending through the cartridge, the opening in communication with a portion of the groove so that an enlarged distal end of a control member of the applicator releasably engages a central member of the clip assembly, the clip assembly including a pair of clip arms, each of the clip arms extending from a proximal end to a distal end, the proximal end of the clip arms connected to one another via the central member slidably received within a channel of a capsule, releasably engaging a connector mechanism of the applicator with a proximal end of the capsule, and moving the clip assembly from an tissue receiving configuration, in which distal ends of the clip arms are separated from one another, to a tissue gripping configuration, in which distal ends of the clip arms are moved toward one another to slide the clip assembly out of the cartridge.

In an embodiment, the opening may be a slot extending into the cartridge laterally of a longitudinal axis of the clip assembly housed therein so that the applicator is inserted therethrough in a lateral direction relative to the clip assembly, an enlarged distal end of a control member of the applicator passed through the opening to be inserted into a lateral slot of a central member via a corresponding slot in the capsule.

In an embodiment, the method may further comprise pivoting the applicator about the enlarged distal end of the control member until the applicator is in axial alignment with the clip assembly.

In an embodiment, the opening may be in axial alignment with the groove so that the distal portion of the applicator is inserted longitudinally into the cartridge until the enlarged end engages of the control member engages the central member.

In an embodiment, the applicator may include a flexible member extending longitudinally from a proximal end to a distal end including the connector mechanism, the control member extending through the flexible member from a proximal end to the enlarged distal end so that moving the control member longitudinally relative to the flexible members moves the clip assembly between the open and tissue gripping configuration.

BRIEF DISCLOSURE

FIG. 2 shows an exploded perspective view of a clip assembly and a cartridge according to the system of FIG. 1;

DETAILED DESCRIPTION

Figure 1:
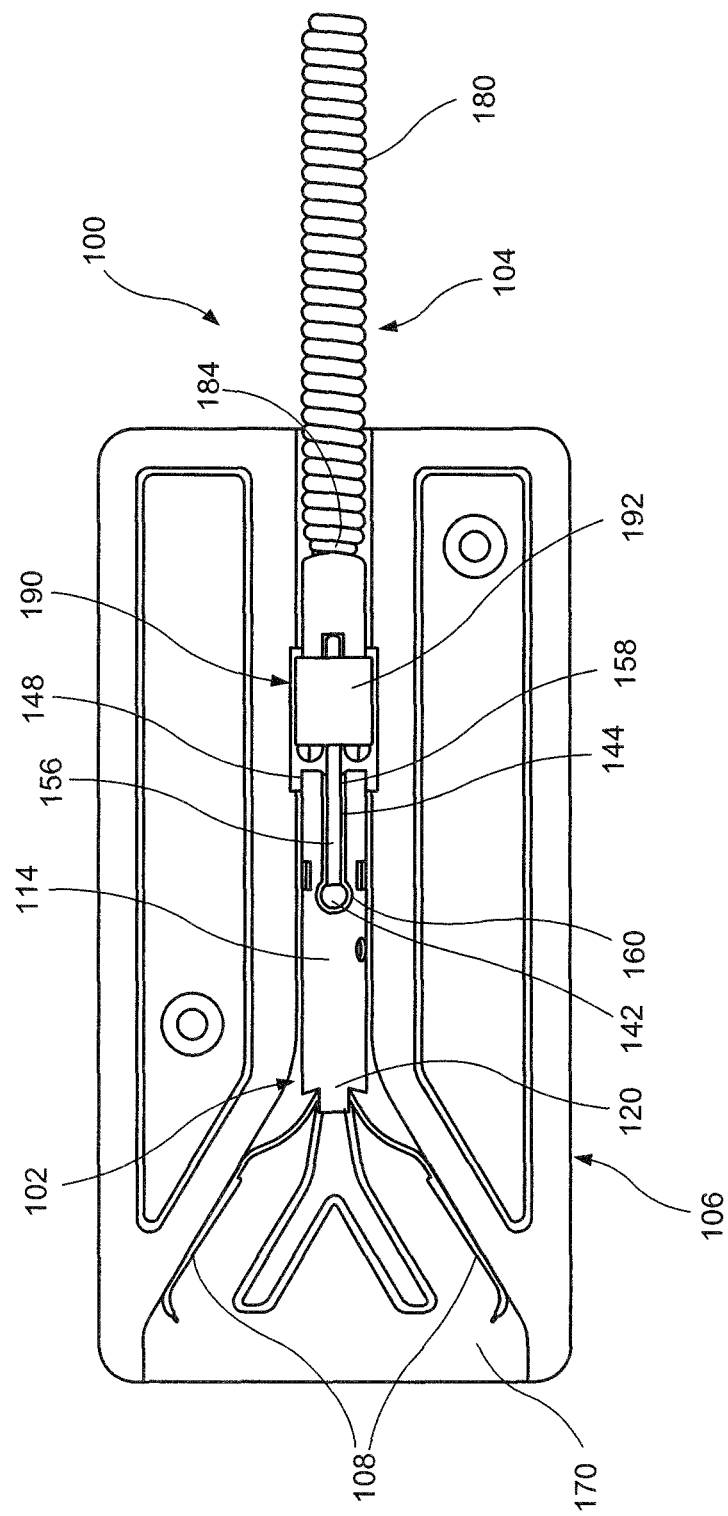
FIG. 1 shows a top plan view of a system according to a first exemplary embodiment of the present disclosure.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. It should be noted that the terms "proximal" and "distal," as used herein, are intended to refer to a direction toward (proximal) and away from (distal) a user of the device.

As shown in FIGS. 1-8, a system 100 according to an exemplary embodiment of the present disclosure comprises a clip assembly 102, an applicator 104 and a cartridge 106. As shown in FIGS. 1 and 2, the clip assembly 102 is loadable onto a distal portion of the applicator 104 prior to insertion of the system 100 into a living body for clipping target tissue. The applicator 104 is configured such that, after deployment of the clip assembly 102 in the living body, a new clip assembly may be loaded onto the applicator 104 so that the same applicator 104 may be used to deliver a new clip assembly 102 to a second portion of tissue in the living body. Each clip assembly 102 according to this embodiment is stored in a cartridge 106, which facilitates loading of the clip assembly 102 onto the applicator 104.

The clip assembly 102 includes a pair of clip arms 108, proximal ends 110 of which may be connected to one another via a central member 112 that is slidably received within a capsule 114. The clip arms 108 are biased to move apart from one another into a tissue receiving configuration when not drawn into the capsule 114 which constrains the clip arms 108, holding them with their distal ends 116 together in a tissue clipping configuration. The central member 112 is longitudinally slidable within the capsule 114 to move the clip arms 108 proximally and distally relative to the capsule 104 to move the clip arms 108 between the tissue receiving and tissue clipping configurations.

Each of the clip arms 108 extends from a proximal end 110 to its distal end 116. The distal end 116 of each of the clip arms 108 according to this embodiment extends laterally inward toward the distal end 116 of the other of the clip arms 108 and may include teeth 122, protrusions or other gripping features to aid in gripping tissue between the clip arms 108 as would be understood by those skilled in the art. The proximal ends 110 of the clip arms 108 include locking tabs 124 extending laterally outward therefrom. As will be described in more detail below, when the clip assembly 102 is deployed, the locking tabs 124 spring outward and lockingly engage a portion of the capsule 114 to prevent the clip arms 108 from being moved proximally out of the capsule 114. This locks the clip arms 108 in the tissue gripping configuration securely gripping any tissue caught between the distal ends 116 of the clip arms 108. A proximal portion of each of the clip arms 108 according to this embodiment includes an opening 126 sized and shaped to receive therein a corresponding protrusion 128 of the central member 112 therein so that the clip arms 108 engage and are aligned with the central member 112. Thus, moving the central member 112 relative to the capsule 114 moves the clip arms 108 proximally and distally relative to the capsule 114, moving the clip arms 108 between the tissue receiving and tissue clipping configurations. The clip arms 108 of this embodiment are biased toward the tissue receiving configuration and are shaped so that, when the central member 112 is drawn proximally into the capsule 114, an interior surface of the capsule 114 engages an exterior surface of, for example, a shoulder 118 of each of the clip arms 108 to draw the clip arms 108 together toward the tissue gripping configuration. When the central member 112 is moved distally relative to the capsule 114, the shoulder 118 of the clip arms 108 extends distally beyond a distal end 120 of the capsule 114 so that the clip arms 108 are permitted to move apart under their natural bias toward the tissue receiving configuration.

Figure 3:
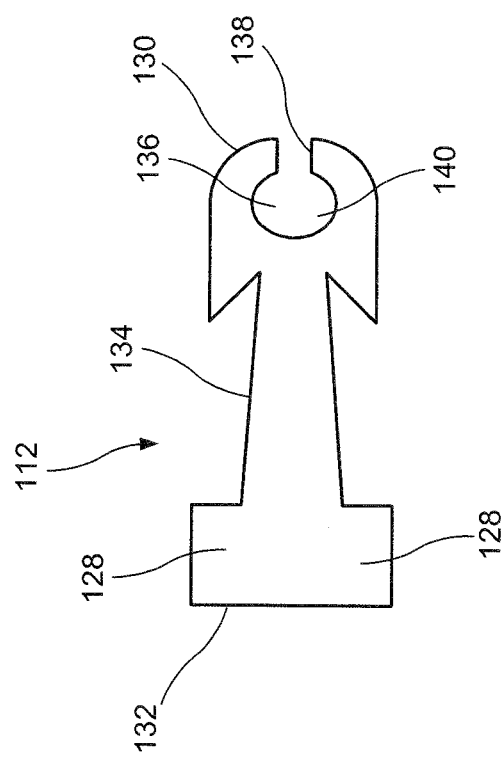
FIG. 3 shows a longitudinal side view of a central member according to the clip assembly shown in FIG. 2.

As shown in FIG. 3, the central member 112 extends longitudinally from a proximal end 130 to a distal end 132 and includes a pair of protrusions 128 extending laterally outward from an exterior surface 134 thereof with each of the protrusions 128 engaging the opening 126 of one of the clip arms 108. The central member 112 includes a slot 136 extending therethrough. The slot 136 extends from an opening 138 at the proximal end 130 to a distal portion 140 which is sized and shaped to receive an enlarged end 142 of a control member 144 of the applicator 104. As will be described in more detail below, the opening 138 at the proximal end 130 has a cross-sectional area (e.g., diameter) smaller than a cross-sectional are of the distal portion 140 of the slot 136 so that an enlarged end 142 of a control member 144 may be inserted into the distal portion 140 which is sized to receive the enlarged end 142. The user may then rotate the control member 144 relative to the capsule 114 to lay the portion of the control member 144 extending proximally from the enlarged distal end 142 into the slot 136. The control member 144 will then remain engaged with the central member 112 until a proximally directed force applied to the control member 144 exceeds a predetermined threshold at which point the enlarged end 142 will be drawn out of the distal portion of the slot 136 spreading apart opposed sides of the central member 112 until the enlarged end 142 is pulled completely out of the slot 136 separating the clipping assembly 102 from the control member 144. As the distal portion 140 is sized to grip the enlarged end 142 of the control member 144 while the proximal opening 138 is sized and shaped to receive a length of the control member 144 extending proximally from the enlarged end 142, movement of the control member 144 controls the movement of the central member 112 relative to the capsule 114.

The capsule 114 extends longitudinally from a proximal end 148 to the distal end 120 and includes a channel 152 extending longitudinally therethrough. The channel 152 is sized and shaped to slidably receive the central member 112 and the clip arms 108 therein. The capsule 114 also includes a slot 156 extending through a portion of the wall thereof from a proximal end 158 corresponding to the proximal end 148 of the capsule 114 to a slot distal end 160. The slot distal end 160 in this embodiment corresponds in size and shape to the distal portion 140 of the slot 136 of the central member 112 so that the enlarged distal end of the control member 144 may be inserted into the distal portion 140 through the capsule 114, while the proximal end 158 corresponds in size and shape to the proximal opening 136 of the slot 136. Of course, those skilled in the art will recognize that the slot 156 may have larger dimensions than the underlying portions of the slot 136 so long as the slot 156 permits the enlarged distal end 142 and the control member 144 to be inserted into the slot 136 through the capsule 114. Thus, when the clip assembly 102 is stored within the cartridge 106, the distal end 160 of the slot 156 of the capsule 114 is aligned with the distal portion 140 of the slot 136 of the central member 112 so that the enlarged end 142 of the control member 144 may be passed laterally through the capsule 114 and into the distal portion 140 of the slot 136 of the central member 112.

The capsule 114 according to this embodiment includes a pair of locking windows 154 extending laterally through a wall thereof for engaging the locking tabs 124 of the clip arms 108, to lock the clip arms 108 in the tissue gripping configuration. Those skilled in the art will recognize that any other feature may be provided on the capsule 114 in place of the windows 154 to mechanically engage the locking tabs 124. The proximal ends 110 of the clip arms 108 according to this embodiment are biased laterally outward so that the locking tabs 124 may ride along the inside surface of the capsule 114 until the locking tabs 124 are drawn proximally into alignment with the locking windows 154. When the locking tabs 124 are drawn to this position, the locking tabs 124 spring outward to lockingly engage the windows 154. Those skilled in the art will understand that this alignment is designed to occur only after or in synchronicity with the withdrawal of the enlarged distal end 142 of the control member 144 from the slot 136 so that the clip assembly 102 is locked in the tissue gripping configuration at the same time that it is separated from the control member 144.

The capsule 114 further includes engaging windows 162 for engaging corresponding engaging features of the applicator 104 when the clip assembly 102 is loaded thereon. The engaging windows 162 extend laterally through the wall of the capsule 114, proximally of the locking windows 154. These engaging windows 162 are sized and shaped to receive, for example, engaging fingers 164 of the applicator 104, as will be described in further detail below. Although the capsule 114 is shown and described as including engaging windows 162 for engaging the applicator 104, the capsule 114 may include other engaging structures so long as the structures releasably engage corresponding engaging features of the applicator 104.

Before it is loaded onto the applicator 104, the clip assembly 102 is stored in a cartridge 106 configured as a storage container comprising a base 166 and a lid 168. The base 166 includes a groove 170 sized and shaped to receive a length of the clip assembly 102 therein. In other words, the groove 170 extends along a length of the base 166 and is sized and shaped to receive the clip assembly 102 in a longitudinal position. More particularly, the groove 170 is sized to house the clip assembly 102 therein in the tissue receiving configuration. When the clip assembly 102 is received within the groove 170, the distal portion 140 of the slot 136 of the central member 112 and the distal end 160 of the slot 156 of the capsule 114 are aligned with one another and the slot 156 of the capsule 114 face away from the base 166. The base 166 is engagable with the lid 168 such that the lid 168 covers the clip assembly 102, encasing the clip assembly 102 in the cartridge 106. The lid 168 includes a groove corresponding to the groove 170 so that when the lid 168 and the base 166 are engaged with one another, the clip assembly 102 is housed within the corresponding grooves 170.

The lid 168 includes a slot 172 extending in alignment with a proximal portion of the groove 170. The slot 172 includes a distal portion 174 sized and shaped to receive the enlarged end 142 of the control member 144 therethrough and a proximal portion 176 extending proximally therefrom sized and shaped to receive a flexible member 180 extending over the control member 144 of the applicator 104 so that, after the enlarged distal end 142 is inserted through the slot 172 into the distal portion 140 of the slot 136, the applicator 104 may be rotated to lay the flexible member 180 into the slot 172 until it is longitudinally aligned with the slot 136 and the distal end of the flexible member 180 may be slid into engagement with the proximal end of the capsule 114. Alternatively, as would be understood by those skilled in the art, the proximal portion 176 of the slot 172 may be sized to receive only the control member 144 so that, as the applicator 104 is rotated to move the flexible member 180 into longitudinal alignment with the slot 136, only the control member 144 enters the slot 172. When the flexible member 180 is longitudinally aligned with the slot 136, the flexible member 180 may be inserted into the cartridge 106 through a proximal opening in the cartridge 106 and may then be slid over the control member 144 until the distal end of the flexible member 180 engages the proximal end of the capsule 114.

A proximal end 178 of the proximal portion 176 is open to an exterior of the lid 166. When the lid 168 is coupled to the base 164 to encase the clip assembly 102 therein, the slot 172 of the lid 168 is aligned with the slots 136, 156 of the central member 112 and capsule 114, respectively, so that the applicator 104 may be coupled to the clip assembly 102 through the lid 168 of the cartridge 106.

Figure 4:
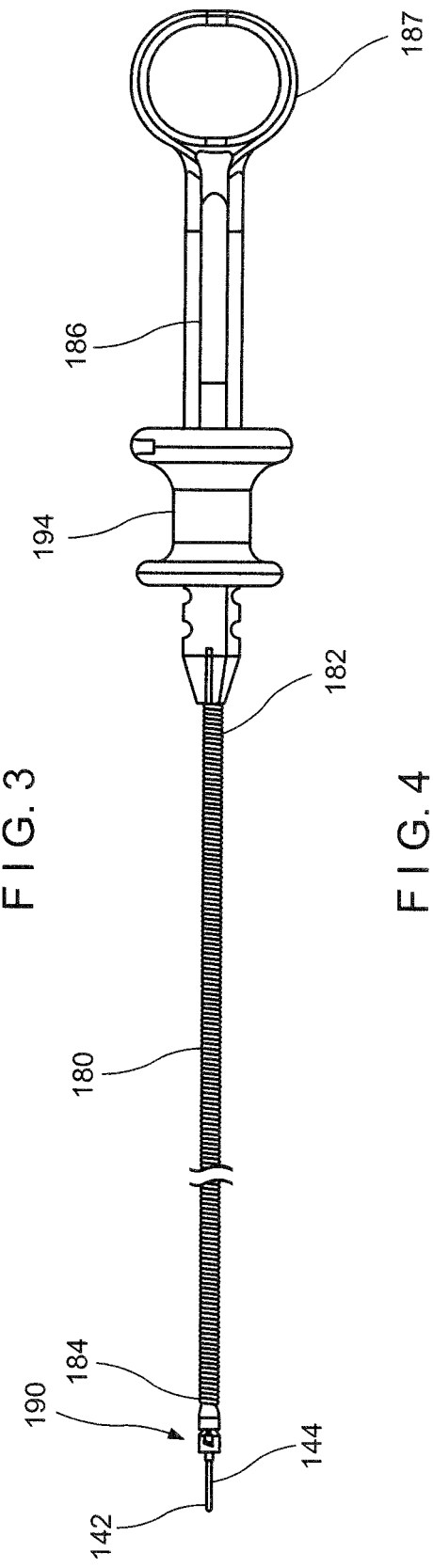
FIG. 4 shows a longitudinal side view of an applicator according to the system of FIG. 1.
Figure 5:
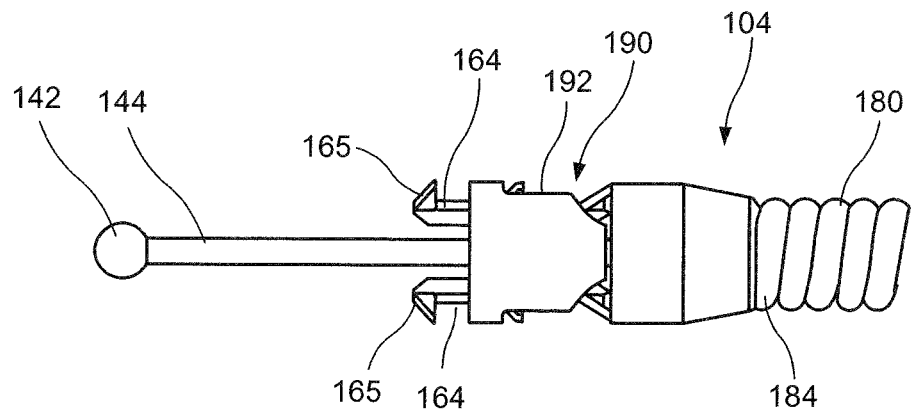
FIG. 5 shows an enlarged, longitudinal side view of a distal portion of the applicator shown in FIG. 4.

As shown in FIGS. 4 and 5, the applicator 104 comprises the flexible member 180 extending longitudinally from a proximal end 182 to a distal end 184. The proximal end 182 is connected to a handle member 186 including an actuator such as the thumb ring 187 and spool 194 described below to operate the control member 144 as described above while the distal end 184 is connected to a connector mechanism 190 including engaging fingers 164 and a capsule release 192 slidable over the flexible member 180 to move the engaging fingers between engaging and disengaging configurations. The engaging fingers 164 include engaging tabs 165 extending laterally outward for engaging the engaging windows 162 of the capsule 114. The flexible member 180 according to this embodiment is formed as a coil of wire although those skilled in the art will understand that any other suitable flexible structure may be employed so long as it is capable of providing a force in compression sufficient to counter the tension that must be placed on the control member 144 to release the control member 144 from the clip assembly 102. The flexible member 180 according to this embodiment is sized and shaped to be passed through a working channel of an endoscope although it may be sized and shaped for use with any other insertion device. The control member 144 extends through the flexible member 180 from a proximal end connected to a slidable spool 194 mounted over the handle member 186 to the enlarged distal end 142. Sliding the spool 194 longitudinally over the handle member 186 moves the control member 144 relative to the flexible member 180. Thus, upon connecting the clip assembly 102 to the applicator 104, the spool 194 may be moved relative to the handle member 186 to control movement of the clip arms 108 between the tissue receiving and tissue gripping configurations. Although the applicator 104 is described as including the spool 194, the applicator 104 may include any of a variety of mechanisms for moving the control member 144 to control movement of the clip arms 108.

Figure 6:
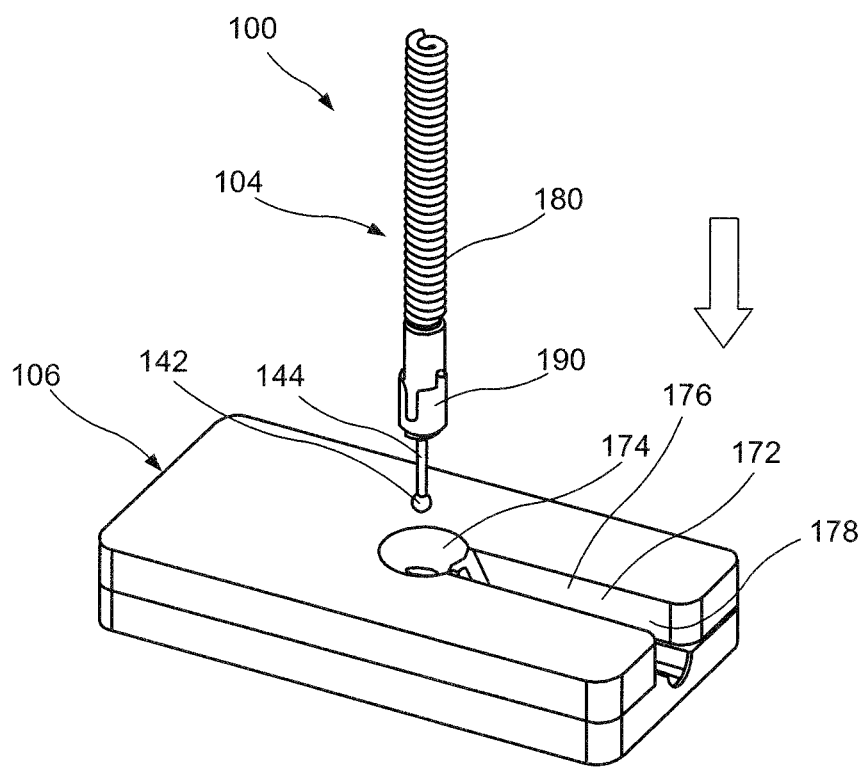
FIG. 6 shows a perspective view of the system of FIG. 1, in a first position.
Figure 7:
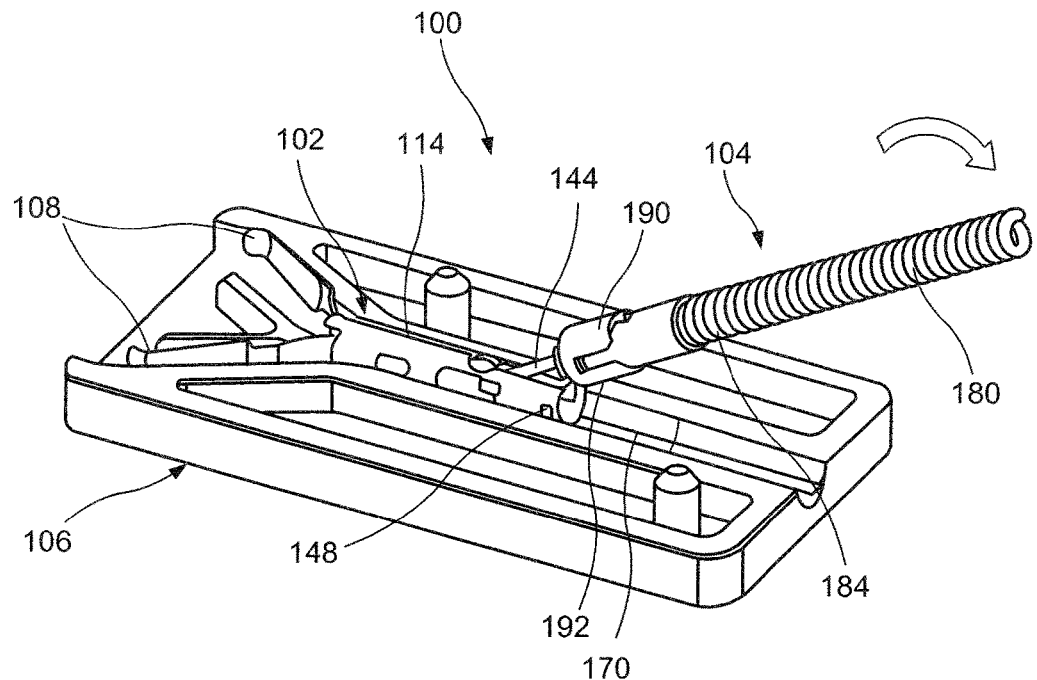
FIG. 7 shows a perspective view of the system of FIG. 1, in a second position, with a lid of the cartridge removed for illustrative purposes.

An exemplary method for connecting the applicator 104 to the clip assembly 102 housed within the cartridge 106 comprises inserting enlarged distal end 142 laterally through the distal portion 174 of the slot 172 of the cartridge 106 and the distal end 160 of the slot 156 of the capsule 114 until the enlarged distal end 142 is received within the distal portion 140 of the slot 136 of the central member 112. As shown in FIG. 6, for this insertion, the applicator 104 may be positioned substantially perpendicular to the cartridge 106 and the clip assembly 102 as the control member 144. Once the enlarged end 142 has been received within slot 136 of the central member 112 via the lateral opening 146, the applicator 104, or at least a distal portion of the flexible member 180, is pivoted about the enlarged end 142, as shown in FIG. 7, until a portion of a length of the control member 144 is received within the proximal opening 138 of slot 136 of the central member 112 and the connector mechanism 190 at the distal end 184 of the flexible member 180 is received within the groove 170 of the cartridge 106.

Figure 8:
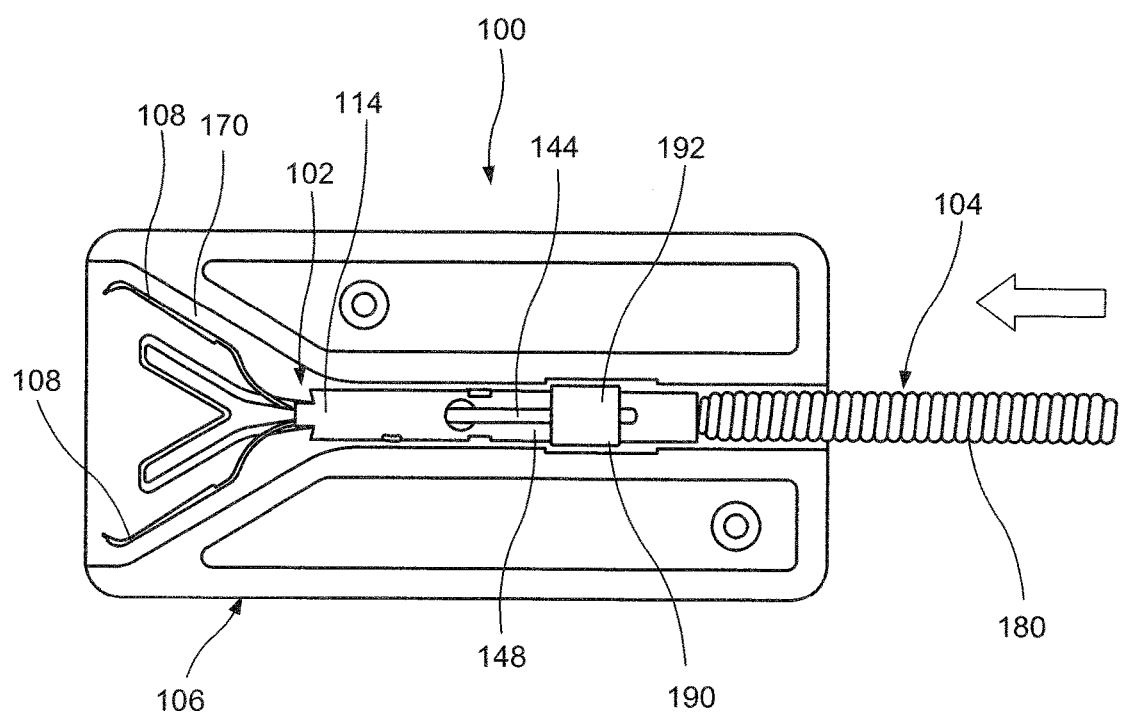
FIG. 8 shows a perspective view of the system of FIG. 1, in a third position, with the lid of the applicator removed for illustrative purposes.

When the control member 144 is positioned within the clip assembly 102, the flexible member 180 and connector mechanism 190 are moved distally relative to the cartridge 106, as shown in FIG. 8, so that the engaging fingers 164 are received within the channel 152 of the capsule 114 and the capsule release 192 extends over the proximal end 148 of the capsule 114. The engaging fingers 164 deform radially inward toward a centerline of the capsule 114 to gain entry within the channel 152 until the engaging tabs 165 of the engaging fingers 164 reach the engaging windows 162 of the capsule 114. At this point, the engaging fingers 164 revert to their biased positions such that the engaging tabs 165 are received within the engaging windows 162 locking the flexible member 180 to the capsule 114. The capsule release 192, which extends over the proximal end 148, holds the engaging tabs 165 in place, locking the applicator 104 to the clip assembly 102. To remove the clip assembly 102 from the cartridge 106, the clip arms 108 may be moved to the closed configuration via the sliding spool 194. Once the clip assembly 102 is in the closed configuration, the entire system 100 is moved proximally relative to the cartridge 106 until the clip assembly 102 is drawn proximally out of the groove 170. Upon loading the clip assembly 102 on the applicator 104 and removing the clip assembly 102 from the cartridge 106, the system 100 is ready for use. It is noted that FIGS. 7 and 8 shows the cartridge 106 with the lid 168 removed for illustration purposes only. In use, the lid 168 will remain engaged with the base 166 so that the cartridge 106 remains closed, enclosing the clip assembly 102 therein until it is withdrawn therefrom for use.

In use, a distal portion of the applicator 104, with the clip assembly 102 connected thereto, is passed through a working channel of an endoscope (or any other insertion device) inserted into the body (e.g., through a natural body lumen) to the site of target tissue. The clip assembly 102 is inserted to the target tissue in the closed configuration to facilitate passage through the working channel. Upon reaching the target tissue, the clip assembly is advanced out of the distal end of the working channel and the clip arms 108 are moved to the tissue receiving configuration by, for example, sliding the spool 194 distally over the handle member 186. The clip arms 108 may be moved between the open and the closed configurations until a target portion of tissue is received between the clip arms 108 as desired. At this point, the clip arms 108 are moved toward the closed configuration by sliding the spool 194 proximally over the handle member 186 to grip the target tissue. When it is confirmed that the desired portion of tissue is gripped between the clip arms 108 (e.g., portions of tissue on opposite sides of a bleeding wound), the control member 144 is drawn further proximally relative to the clip assembly 102 (via the spool 194) to lock the clip assembly 102 in the closed configuration. That is, the clip arms 108 are drawn further proximally into the capsule 114 until locking tabs 124 at the proximal ends 110 thereof engage the locking windows 154.

As clip assembly 102 is locked in the closed configuration, the control member 144 is drawn farther proximally relative to the clip assembly 102 until a force applied by the enlarged end 142 against the slot 136 of the central member 112 exceeds a threshold force, disengaging the control member 144 from the central member 112 and the clip assembly 102. As the control member 144 is disengaged from the central member 112, the enlarged end 142 contacts a portion of the capsule release 192, moving the capsule release 192 proximally relative to the engaging fingers 164. Movement of the capsule release 192 relative to the engaging fingers 164 draws the engaging fingers 164 radially inward disengaging the engaging tabs 165 from the engaging windows 162 of the capsule 114 and separating the capsule 114 and the clip assembly 102 from the flexible member 180. The clip assembly 102 is then left in the body until natural healing processes progress and the clip assembly 102 is sloughed off the target tissue. The applicator 104 may then be withdrawn from the body and a new clip assembly 102 may be inserted onto the distal end of the flexible member 180 in the same manner described above. The device may then be used to clip a second portion of tissue in the same manner and the process may be repeated using the same applicator 104 as many times as need.

Figure 9:
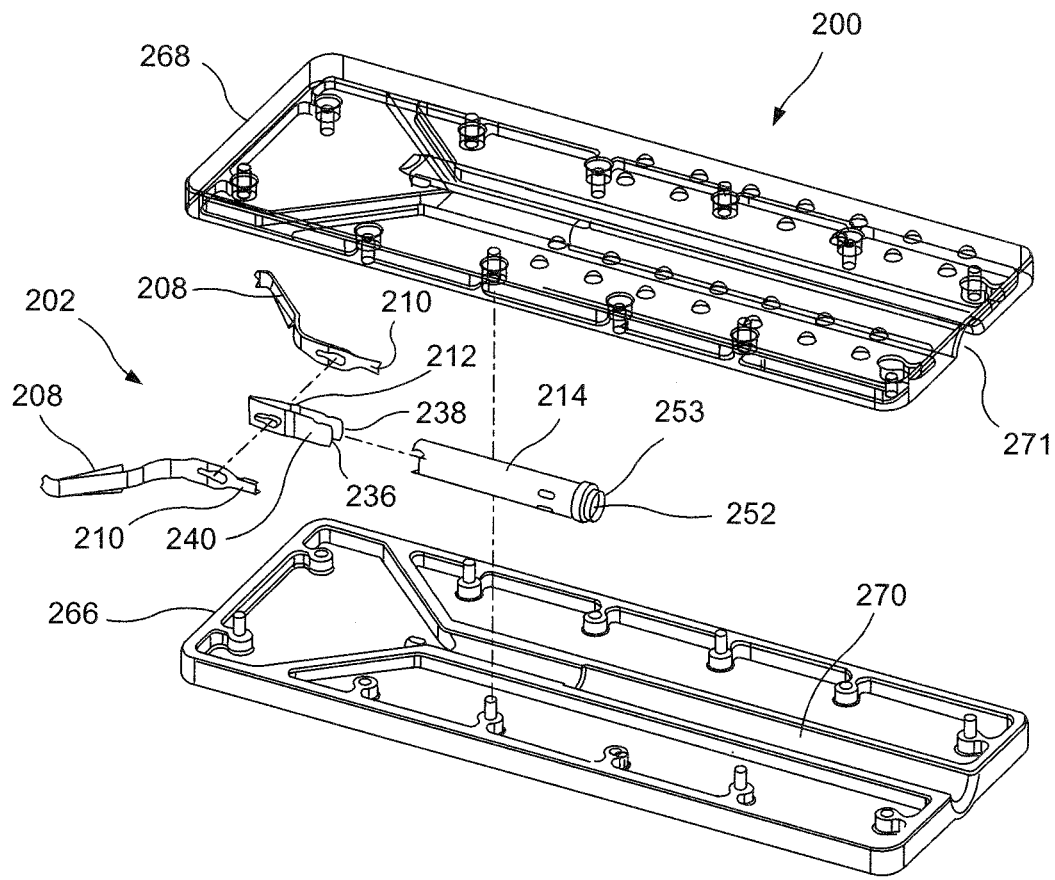
FIG. 9 shows an exploded perspective view of a system according to a second exemplary embodiment of the present disclosure.
Figure 10:
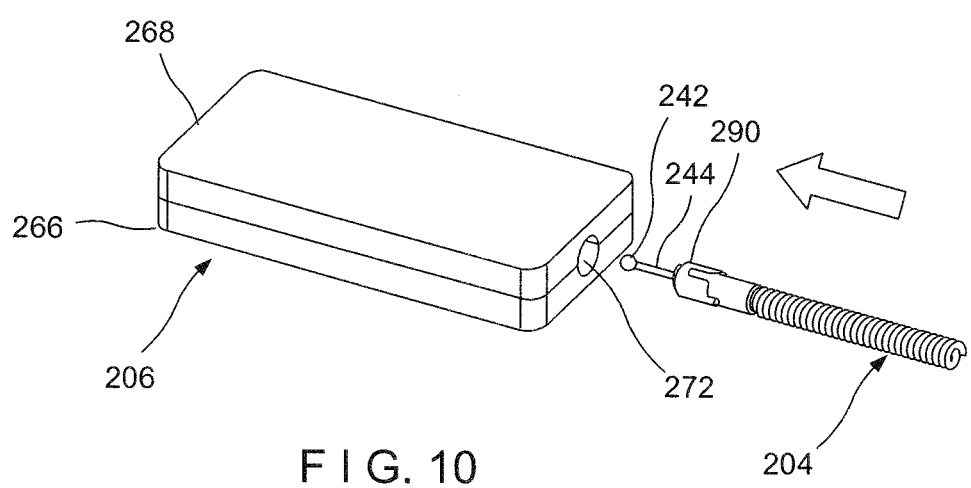
FIG. 10 shows another perspective view of the system of FIG. 9.

As shown in FIGS. 9 and 10, a system 200 according to another exemplary embodiment of the present disclosure comprises a clip assembly 202 loadable on a distal portion of an applicator 204 in the same manner described above except for the differences outlined below. Similarly to the system 100, the clip assembly 202 is housed within a cartridge 206 configured so that a portion of the applicator 204 may be inserted therein to connect (e.g., load) the clip assembly 202 and the applicator 204 to one another. Rather than a lateral approach through a lid 268 of the cartridge 206, however, the applicator 204 is connected to the clip assembly 202 via an axial approach relative to the clip assembly 202 and the cartridge 206.

The clip assembly 202 is substantially similar to the clip assembly 102, described above in regard to the system 100, comprising a pair of arms 208, proximal ends 210 of which are connected to a central member 212 that is slidably received within a capsule 214 to move the arms 208 between tissue receiving and tissue gripping configurations as described above. The capsule 214, does not have a slot extending through a wall thereof. Rather, an enlarged end 242 of a control member 244 of the applicator 204 is inserted into a distal portion 240 of a lateral slot 236 of the central member 212 via a proximal opening 253 of a channel 252 of the capsule 214. When the control member 244 is pushed distally into the capsule 214 and the central member 212 beyond a predetermined threshold value, a proximal opening 238 of the slot 236 of the central member 212 deforms to permit the enlarged end 242 of the control member 244 to be passed therethrough into the distal portion 240. In other words, portions of the central member 212 defining the slot 236 are separated from one another to permit the enlarged end 242 to be passed through the proximal opening 238 into the distal portion 240. Once the enlarged end 242 is received within the distal portion 240, the proximal opening 238 of the slot 236 reverts to its original size, holding the enlarged end 242 of the control member 244 in the distal portion 240.

The cartridge 206 may be substantially similar to the cartridge 106 comprising a base 266 defining a groove 270 sized and shaped to accommodate the clip assembly 202. The lid 268 may include a groove 271 corresponding to the groove 270 so that the clip assembly 202 may be housed therein between the base 266 and the lid 268. The lid 268 however, does not require a lateral slot formed therein in alignment with the grooves 270, 271. Rather, the applicator 204 may be connected to the clip assembly 202 by inserting a distal portion 290 of the applicator 204 through a proximal opening 272 defined via the corresponding grooves 270, 271. Thus, the applicator 204 may be inserted into the cartridge 206 via the axial approach to connect the applicator 204 to the clip assembly 202, as described above. Once connected or loaded to the applicator 204, the clip assembly 202 may be removed from the cartridge 206 in a manner substantially similar to the system 100 described above. The loaded clip assembly 202 may be used to clip tissue in a manner substantially similar to the clip assembly 102.

It will be apparent to those skilled in the art that various modifications may be made in the present disclosure, without departing from the scope of the disclosure.

What is claimed is:

1. A system for treating tissue, comprising:
a clip assembly including a pair of clip arms, each of the clip arms extending from a proximal end to a distal end, the proximal ends of the clip arms connected to one another via a central member slidably received within a channel of a capsule to be moved between an open configuration, in which distal ends of the clip arms are separated from one another, and a closed configuration, in which distal ends of the clip arms are moved toward one another;
a cartridge for encasing the clip assembly including a groove formed therein to accommodate the clip assembly and an opening extending therein to in communication with a portion of the groove such that the groove is open to an exterior of the cartridge via the opening; and
an applicator releasably connectable to the central member to move the clip assembly between the open configuration and the closed configuration, a distal portion of the applicator insertable through the opening of the cartridge to reversibly engage and disengage from the central member while the central member remains intact within the capsule,
wherein the capsule includes a locking feature formed in a wall thereof for engaging an engaging tab at the proximal end of one of the clip arms to lock the clip arms in the closed configuration.

2. The system of claim 1, wherein the clip arms are biased in the open configuration.

3. The system of claim 1, wherein the opening of the cartridge is a slot extending therein laterally relative to a longitudinal axis of the clip assembly.

4. The system of claim 1, wherein the opening of the cartridge extends therein in axial alignment with a longitudinal axis of the clip assembly.

5. The system of claim 1, wherein each of the clip arms comprises an opening, and the central member comprises a pair of protrusions extending laterally outwardly from the central member for engaging the openings of the clip arms.

6. The system of claim 1, wherein the locking feature is a locking window extending through the wall.

7. The system of claim 1, wherein the applicator includes a flexible member extending longitudinally from a proximal end which, when the system is inserted into a living body, is external to the living body to remain accessible to a user, to a distal end including a connector mechanism for connecting to a proximal end of the capsule, a control member extending through the flexible member from a proximal end accessible to the user to an enlarged distal end releasably connectable to the central member.

8. The system of claim 7, wherein the central member includes a lateral slot extending therethrough, the lateral slot extending from an opening at a proximal end thereof to a distal portion of the lateral slot, the opening at the proximal end having a smaller cross-sectional area than the distal portion of the lateral slot and the distal portion of the lateral slot being sized and shaped to accommodate the enlarged distal end of the control member therein.

9. The system of claim 7, wherein the capsule includes a capsule slot extending laterally through a wall thereof longitudinally from the proximal end of the capsule to a distal end of the capsule slot, the distal end of the capsule slot being sized and shaped to permit passage of the enlarged distal end of the control member therethrough.

10. The system of claim 7, wherein the capsule includes engaging windows for receiving a portion of the connector mechanism of the applicator.

11. The system of claim 10, wherein the connector mechanism includes a plurality of fingers biased radially outward to engage the engaging windows when the plurality of fingers are received within the channel of the capsule.

12. The system of claim 11, wherein the connector mechanism further includes a capsule release slidable over the plurality of fingers to be moved between a first configuration in which, when the plurality of fingers engage the engaging windows, the capsule release is mounted over the proximal end of the capsule to maintain the connection between the applicator and the clip assembly, and a second configuration in which the capsule release is slid proximally relative to the plurality of fingers to deform the fingers radially inward to release the fingers from the engaging windows.

13. The system of claim 7, wherein the applicator includes a handle member connected to the proximal end of the flexible member and a spool slidably mounted over the handle member and connected to the proximal end of the control member to move the control member longitudinally relative to the flexible member.

14. A method for loading a clip assembly onto an applicator, comprising:

inserting a distal portion of an applicator through an opening of a cartridge housing a clip assembly, the clip assembly housed within a groove extending through the cartridge, the opening in communication with a portion of the groove so that an enlarged distal end of a control member of the applicator releasably engages a central member of the clip assembly, the clip assembly including a pair of clip arms, each of the clip arms extending from a proximal end to a distal end, the proximal ends of the clip arms connected to one another via the central member slidably received within a channel of a capsule, wherein the applicator reversibly engages and disengages from the central member while the central member remains intact within the capsule;

releasably engaging a connector mechanism of the applicator with a proximal end of the capsule; and moving the clip assembly from a tissue receiving configuration, in which distal ends of the clip arms are separated from one another, to a tissue gripping configuration, in which distal ends of the clip arms are moved toward one another to slide the clip assembly out of the cartridge, wherein the opening is a slot extending into the cartridge laterally of a longitudinal axis of the clip assembly housed therein so that the applicator is inserted therethrough in a lateral direction relative to the clip assembly, an enlarged distal end of a control member of the applicator passed through the opening to be inserted into a lateral slot of the central member via a corresponding slot in the capsule.

15. The method of claim 14, further comprising pivoting the applicator about the enlarged distal end of the control member until the applicator is in axial alignment with the clip assembly.

16. The method of claim 14, wherein the opening is in axial alignment with the groove so that the distal portion of the applicator is inserted longitudinally into the cartridge until the enlarged end of the control member engages the central member.

17. The method of claim 14, wherein the applicator includes a flexible member extending longitudinally from a proximal end to a distal end including the connector mechanism, the control member extending through the flexible member from a proximal end to the enlarged distal end so that moving the control member longitudinally relative to the flexible member moves the clip assembly between the tissue receiving and tissue gripping configurations.

* * * * *